United States Patent [19]

Schnabel et al.

[11] Patent Number: 4,758,508

[45] Date of Patent: * Jul. 19, 1988

[54] ANALYTICAL PROCESS AND AGENTS FOR THE DETECTION OF ESTEROLYTIC AND/OR PROTEOLYTIC ENZYMES

[75] Inventors: Eugen Schnabel, Wuppertal, Fed. Rep. of Germany; James Travis, Athens, Ga.; A. Christopher Skjold, Elkhart, Ind.

[73] Assignee: Miles Inc., Elkhart, Ind.

[*] Notice: The portion of the term of this patent subsequent to Jul. 5, 2005 has been disclaimed.

[21] Appl. No.: 710,423

[22] Filed: Mar. 11, 1985

[30] Foreign Application Priority Data

Apr. 6, 1984 [DE] Fed. Rep. of Germany ....... 3413118

[51] Int. Cl.$^4$ .......................... C12Q 1/44; C12Q 1/38
[52] U.S. Cl. ........................................ 435/19; 435/23; 435/805; 435/810
[58] Field of Search ...................... 435/19, 20, 21, 23, 435/24, 805, 810

[56] References Cited

U.S. PATENT DOCUMENTS

| | | | |
|---|---|---|---|
| 4,212,939 | 7/1980 | Myrick et al. | 435/19 |
| 4,296,202 | 10/1981 | Berger et al. | 435/29 |
| 4,299,917 | 11/1981 | Berger et al. | 435/23 X |
| 4,331,760 | 5/1982 | Berger et al. | 435/19 |
| 4,469,789 | 9/1984 | Berger et al. | 435/23 |
| 4,499,185 | 2/1985 | Skjold et al. | 435/19 |
| 4,551,428 | 11/1985 | Berger et al. | 435/23 X |

OTHER PUBLICATIONS

Chem. Abs. 97: 66122a (1982).
Magnusson, "Bovine Prothrombin and Thrombin" in Colowick et al., *Methods in Enzymology*, vol. XIX, Academic Press, N.Y. 1970, pp. 158-170.

*Primary Examiner*—Esther M. Kepplinger
*Assistant Examiner*—Shawn P. Foley
*Attorney, Agent, or Firm*—Roger N. Coe

[57] ABSTRACT

Agent for the detection of esterolytic and/or proteolytic enzymes, containing (a) an amino acid ester or peptide ester of a phenol, as the chromogenic enzyme substrate, and (b) an alcohol as the substance which accelerates the enzymatic cleavage of the amino acid ester bond or peptide ester bond of component (a), characterized in that it contains a salt as the accelerating substance.

7 Claims, No Drawings

ANALYTICAL PROCESS AND AGENTS FOR THE DETECTION OF ESTEROLYTIC AND/OR PROTEOLYTIC ENZYMES

The present invention relates to agents for analytical detection of esterolytic and/or proteolytic enzymes, for example in body fluids, the esters being incorporated into test agents, in particular test strips, in a suitable manner. Besides chromogenic enzyme substrates (aminoacid esters or peptide esters of suitable phenols) and, if appropriate, diazonium salts which couple with the phenols to form a colour, the agents according to the invention also contain salts as accelerators for the enzymatic cleavage of the aminoacid esters or peptide esters. The agents are preferably used for the detection of leucocytes, in particular in urine.

The detection of leucocytes in body fluids, in particular in urine, is of great importance in the diagnostics of diseases of the kidneys and of the urogenital tract. This detection was originally carried out by counting the leucocytes in the noncentrifuged urine or in the urine sediment. In both methods, only intact leucocytes can be recorded. However, it is known that the rate of leucocytelysis is subject to wide variations, depending on the urine medium; thus, for example, in strongly alkaline urines the leucocyte half-life is only 60 minutes. This means that the leucocyte counts determined are too low. Apart from this lysis error, quantitative microscopic determination of the leucocytes in the noncentrifuged, homogenised urine gives very accurate values in the counting chamber. Nevertheless, this method is only rarely used in practice, since it is laborious and time-consuming and requires trained personnel.

The preferred process for leucocyte determinations in the urine in medical practice was therefore the so-called field of view method in the urine sediment. For this, the sample (sediment) first had to be obtained by centrifugation. However, other constituents of the urine were also thereby concentrated, and these - such as, for example, salts and epithelial cells - make microscopic counting of the leucocytes considerably more difficult. A varying sediment content, inhomogeneities of the sediment and a different optical design of the microscopes led to relatively large errors (up to several hundred percent) in stating the leucocyte count.

In order to avoid these difficulties, several attempts have already been made to use enzymatic reactions as the detection principle for leucocytes in various body fluids, since leucocytes have a widely spread enzyme spectrum.

Thus, for example, agents for the detection of leucocytes in body fluids are known from German Offenlegungsschriften (German Published Specification) Nos. 2,826,965 and 2,836,644, in which the esterolytic and/or proteolytic activity present in the leucocytes is utilised for analytical purposes. Sulphonphthaleine esters or azo dyestuff esters are used as substrates for the leucocyte esterases and/or proteases. The dyestuffs released in the enzymatic reaction are then determined by known methods. However, the agents described in these publications are still too insensitive for practical purposes, since their reaction times are too long with low leucocyte concentrations.

Various methods for the detection of proteases and esterases are also known from histochemical and cytochemical enzymology (compare, for example, A.G.E. Pearse, Histochemistry, Theoretical and Applied, 3rd edition, Churchill Livingstone, Edinburgh-London-New York 1968). In general, colourless or slightly coloured esters are used for the detection, these being split by the enzymes into a colourless acid and a similarly colourless alcohol (phenol) component. The phenol component is then converted into coloured products in a subsequent reaction, for example by coupling with diazonium salts or by oxidation. F. Schmalzl and H. Braunsteiner, for example, describe in Klin. Wschr. 46, 642 (1968) a specific cytochemical leucocyte esterase detection with naphthol-AS-D-chloroacetate as the substrate and a diazonium salt which forms a coloured azo compound with the naphthol liberated.

However, two-component systems of this type have proved to be unsuitable for rapid and simple detection of leucocytes in body fluids, such as, for example, in the urine, since they are much too insensitive: samples containing 5,000 leucocytes/$\mu$l still do not give a reaction.

British Patent No. A-1,128,371 and European Patent No. A-12,957 describe the use of indoxyl and thioindoxyl esters as chromogenic substrates for the detection of hydrolytic enzymes in body fluids. On enzymatic cleavage of the substrate, free indoxyl is formed, which is subsequently oxidised to the easily detectable blue dyestuff indigo. A commercially available test based on European Patent No. A-12,957 consists of a strip of filter paper impregnated with N-tosyl-L-alanine indoxyl ester. When the test strip is immersed in a urine sample containing leucocytes, it turns blue in colour. However, the long waiting time (about 15 minutes) before the end colouration is reached and the test can be evaluated is a considerable disadvantage of this product.

European Patent No. A-14,929 describes various accelerators (pyridine derivatives; imidazole derivatives; alcohols; metal complexes) for the enzymatic cleavage reaction. However, the relatively long time before complete oxidation of the indoxyl and the low sensitivity of the test (detection limit: a few thousand leucocytes/$\mu$l) remain a disadvantage. The same applies to the use of esters of leuco-indoanilines as substrates for leucocyte enzymes according to European Patent No. A-34,323.

European Patent No. A-39,880 provides a combination of the substrates according to European Patent Nos. A-12,957 and 14,929 with the detection principle of coupling with diazonium salts which has been discussed above. Although it is possible considerably to reduce the detection limits for leucocytes in this way, the detection sensitivity of 15-20 leucocytes/$\mu$l which is desired for use in practice is still not achieved.

The object of the present invention was thus to discover new activators for ester-cleaving enzymes which, as a result of acceleration of the enzymatic cleavage of the substrates by the leucocyte enzymes, permit sensitive and more rapid detection of the leucocytes in urine. This object is achieved by using salts to the reagent system.

As has been found, surprisingly, the cleavage of the chromogenic substrates by leucocyte enzymes is considerably accelerated by the addition of salt, or the action of activators already present in the test system is potentiated.

The invention relates to agents for the detection of esterolytic and/or proteolytic enzymes, containing (a) an aminoacid ester or peptide ester of a phenol, as the chromogenic enzyme substrate, (b) a substance which accelerates the enzymatic cleavage of the aminoacid ester bond or peptide ester bond of component (a), if appropriate (c) a diazonium salt, if appropiate (d) a buffer, and if appropriate (e) a carrier and/or the usual additives, which are characterised in that a salt is used as the accelerating substance, if appropriate together with other activators.

Finally, the invention also relates to a process for the detection of esterolytic and/or proteolytic enzymes in liquid samples, in particular body fluids, which is characterised in that the sample is brought into contact with the agent according to the invention and the colour reaction which occurs is determined.

According to the invention, salts which have an accelerating action are, in particular, salts of monovalent and divalent cations of the alkali metals and alkaline earth metals, such as, for example, $Li^+$, $Na^+$, $K^+$ and $Mg^{++}$. Preferred anions of the activating salts are monovalent, divalent or trivalent organic or inorganic anions. Anions which may be mentioned in particular are halides and pseudohalides, sulphates and phosphates, and the ions of organic acids, such as acetic acid, trifluoroacetic acid, toluenesulphonic acid and succinic acid.

According to the invention, the concentrations of the salts in the test solutions are preferably between 0.05 M and 2 M, particularly preferably between 0.1 and 1 M.

In the formulations for impregnation of carriers (in the under described production of test devices), the salts are preferably dissolved in amounts of 0.01 M to 2 M, particularly preferably 0.1 to 1 M.

The salts to be used according to the invention accelerate the enzymatic cleavage of the substrates described in European Patent Nos. A-7,407, 8,428, 12,557, 14,929, 34,323 and 39,880 by the leucocyte enzymes, as well as the cleavage of the substrates which have already been described previously (G. Gomori, J. Histochem. Cytochem. 6 469 (1953); H. Löffler, Klin. Wochenschr. 39, 1120 (1961); L. Visser and E. Blout, Fed. Proc. 28, 407 (1969) and Biochim. Biophys. Acta 268, 257 (1972) and R. Sweetman and L. Ornstein, J. Histochem. Cytochem. 23, 327 (1974)).

The preferred chromogenic substrates in the agents according to the invention also include the compounds described in a parallel Application, of the general formula

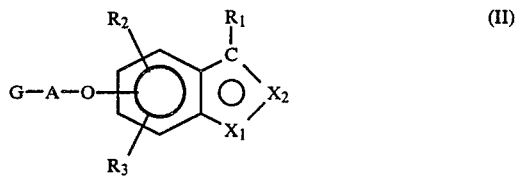

(II)

in which $X_1$ and $X_2$ are identical or different and denote nitrogen or sulphur, with the proviso that $X_1$ and $X_2$ do not simultaneously represent sulphur;

$R_1$ represents hydrogen or an optionally branched alkyl group which has 1 to 6 carbon atoms and can optionally be halogen or hydroxyl;

$R_2$ and $R_3$ are identical or different and represent hydrogen, $C_1-C_6$-alkyl groups, $C_1-C_6$-alkoxy groups, $C_1-C_6$-acyl groups, halogen, trifluoromethyl, nitro, $SO_3H$, cyano, $C_1-C_8$-acylamino groups, $C_1-C_6$-dialkylamino groups or $C_6-C_{10}$-aryl groups, which can in turn be further substituted by $C_1-C_6$-alkyl groups, $C_1-C_6$-alkoxy groups, halogen, cyano, nitro, trifluoromethyl, $SO_3H$, $C_1-C_6$-acyl groups or $C_1-C_6$-dialkylamino groups, or $R_2$ and $R_3$ together form a fused-on aromatic ring, preferably a benzene ring, which can in turn be substituted by 1 or 2 radicals $R_2$;

A denotes an aminoacid radical or peptide radical; and

G represents hydrogen or, preferably, a nitrogen-protective group which is usual in peptide chemistry or derived from such a group.

Preferred compounds of the general formula (II) are those in which $X_1$ represents sulphur and $X_2$ represents nitrogen. Compounds of the formula (II) in which $R_1$ represents hydrogen, and those in which $R_2$ and $R_3$, which are identical or different, represent hydrogen, $C_1-C_2$-alkyl, $C_1-C_2$-alkoxy, halogen, $C_1-C_4$-dialkylamino groups or benzene radicals are furthermore preferred.

The ester radical in the compounds of the formula (II) is particularly preferably in the 5-position.

Other chromogenic substrates which are preferred according to the invention are the compounds likewise described in a parallel Application, of the general formula

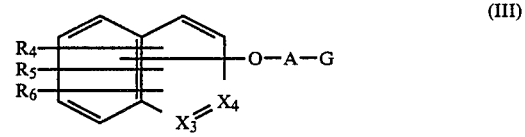

(III)

in which $X_3$ and $X_4$ represent N or CH, with the proviso that in each case either $X_3$ or $X_4$ represent N;

$R_4$, $R_5$ and $R_6$ are identical or different and represent hydrogen, $C_1-C_6$-alkyl groups, $C_1-C_6$-alkoxy groups, $C_1-C_6$-acyl groups, halogen, trifluoromethyl, nitro, $SO_3H$, cyano, $C_1-C_8$-acylamino groups, $C_1-C_6$-dialkylamino groups or $C_6-C_{10}$-aryl groups, which can in turn be further substituted by $C_1-C_6$-alkyl groups, $C_1-C_6$-alkoxy groups, halogen, cyano, nitro, trifluoromethyl, $SO_3H$, $C_1-C_6$-acyl groups or $C_1-C_6$-dialkylamino groups, or $R_5$ and $R_6$ together form a fused-on aromatic ring, preferably a benzene ring, which can in turn be substituted by 1 or 2 radicals $R_4$; and A and G have the meaning given above in the case of the formula (II).

In the compounds according to the general formula (III), $X_3$ preferably represents CH and $X_4$ preferably represents nitrogen. $R_4$, $R_5$ and $R_6$, which can be identical or different, preferably represent hydrogen, $C_1-C_4$-alkyl, $C_1-C_4$-alkoxy, acylamino (where the acid radical can be aliphatic or aromatic with 1-6 C atoms), $C_1-C_4$-dialkylamino, nitro, cyano, halogen, or aryl, which is optionally substituted by $C_1-C_4$-alkyl, $C_1-C_4$-alkoxy or halogen. Particular preferably, $R_4$, $R_5$ and $R_6$ are hydrogen, $C_1-C_4$-alkyl, phenyl or halogen, or $R_5$ and $R_6$ together form a fused-on benzene ring.

Suitable chromogenic substrates for the agents according to the invention are moreover also compounds of the general formula

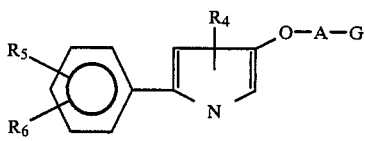

(IV)

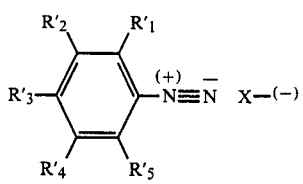

(V)

wherein
R$_4$, R$_5$, R$_6$, A and G have the meaning given above in the case of formula (III).

In the general formulae (II), (III) and (IV), G—A— preferably represents a radical of the general formula

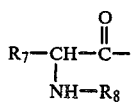

in which
R$_7$ represents hydrogen or an optionally branched alkyl, cycloalkyl or aryl radical which has 1-15 C atoms, preferably 1-9 C atoms, and is optionally substituted by a hydroxyl, mercapto or carboxyl group, and R$_8$ represents hydrogen or, preferably, —CO—alkyl, —CO—aralkyl, —CO—aryl, —SO$_2$-alkyl or —SO$_2$-aryl, the alkyl radicals being straight-chain or branched with 1-9 C atoms, preferably 1-6 C atoms, and the aryl radicals preferably representing benzene rings, which are optionally substituted by C$_1$-C$_4$-alkyl groups, C$_1$-C$_4$-alkoxy groups or halogen.

G—A—particularly preferably represents a radical, provided with a customary nitrogen-protective group, of a naturally occurring aminoacid or of a peptide of 2 to 8 such aminoacids.

The aminoacid radicals can be in their L- or D-form or in their racemic form here. Particularly preferred radicals are those of glycine, alanine, valine, leucine, isoleucine, phenylalanine and tyrosine, the L-form being particularly preferred in each case. Any free hydroxyl group present can be acylated, preferably acetylated.

A peptide radical in the definition of A is to be understood as meaning, for example, di-, tri-, tetra- and pentapeptides, preferably di- and tri-peptides, preferred possible aminoacid components being the abovementioned aminoacids.

The substrates of the general formulae (II), (III) and (IV) are obtained by reacting the corresponding phenols with aminoacids or peptides of the general formula

G—A—OH in which
G and A have the abovementioned meaning, or suitable reactive derivatives thereof, by methods customary in peptide chemistry.

Examples of suitable reactive derivatives are the acid chlorides and the mixed anhydrides usually employed in peptide synthesis, for example with ethyl chloroformate or active esters, such as, for example, pentachlorophenyl esters or N-hydroxybenzotriazole esters.

The agents according to the invention preferably contain, as colour-forming agents which react with the phenols (liberated during enzymatic cleavage), diazonium salts of the general formula in which
R'$_1$ denotes a lower alkyl, a lower alkoxy, a lower alkylmercapto, a hydroxy, nitro, cyano, trifluoromethyl, C$_1$-C$_8$-alkylsulphonamido, arylsulphonamido, C$_1$-C$_8$-alkylsulphone, arylsulphone, sulphonic acid or carboxylic acid, an N-morpholino, an N-thiomorpholino, an N-pyrrolidino, an optionally N'-alkylated N-piperazino or N-piperidino group, halogen or hydrogen, R'$_3$ denotes a lower alkyl, a lower alkoxy, an aryloxy, a lower alkylmercapto, alkylamino or dialkylamino, a hydroxyl, nitro, cyano, C$_1$-C$_8$-alkylsulphonamido, arylsulphonamido, C$_1$-C$_8$-alkylsulphone, arylsulphone, sulphonic acid or carboxylic acid, an N-morpholino, N-thio-morpholino or N-pyrrolidino, an optionally N'-alkylated N-piperazino or N-piperidino or phenylamino group, a phenyl group which is optionally substituted by a lower alkyl or lower alkoxy radical, halogen or hydrogen, R'$_2$, R'$_4$ and R'$_5$, which can be identical or different, each denote a lower alkyl, a lower alkoxy, nitro, C$_1$-C$_8$-alkylsulphonamido, arylsulphonamido, C$_1$-C$_8$-alkylsulphone, arylsulphone, sulphonic acid or carboxylic acid or a lower alkyl mercapto group, halogen or hydrogen and X denotes a stabilising anion, it being possible in each case for two adjacent radicals R'$_1$ to R'$_5$ to be cyclised to form a benzene ring which is optionally substituted by halogen, a C$_1$-C$_6$-alkyl, a C$_1$-C$_6$-alkoxy or a nitro, sulphonic acid or carboxylic acid group, so that a diazonium salt of the naphthalene series is formed.

Preferably, in the general formula (V)
R'$_1$ represents C$_1$- to C$_4$-alkyl, C$_1$-C$_4$-alkoxy, hydroxyl, nitro, halogen or hydrogen, R'$_3$ represents a C$_1$- to C$_4$-alkyl, C$_1$-C$_4$-alkoxy, aryloxy, C$_1$-C$_4$-alkylamino, C$_1$-C$_4$-dialkylamino, nitro, C$_1$-C$_4$-alkylsulphonamido, arylsulphonamido, C$_1$-C$_4$-alkylsulphone, arylsulphone, N-morpholino, N-pyrrolidino, phenylamino or sulphonic acid group or hydrogen; and R'$_2$, R'$_4$ and R'$_5$, which can be identical or different, represent C$_1$- to C$_4$-alkyl, C$_1$- to C$_4$-alkoxy, C$_1$- to C$_4$-alkylamino, C$_1$ to C$_4$-dialkylamino, nitro, C$_1$- to C$_4$-alkylsulphonamido, arylsulphonamido or sulphonic acid group, halogen or hydrogen.

In each case 2 adjacent radicals R'$_1$ to R'$_5$ can here optionally be cyclised to give a benzene ring which is optionally substituted by halogen or a C$_1$ to C$_4$-alkyl or C$_1$- to C$_4$-alkoxy or a nitro or sulphonic acid group.

In the context of the formula (V), aryl in each case represents an aromatic radical which has 6 to 12 C atoms, preferably 6 C atoms, and is optionally substituted by halogen or a C$_1$-C$_4$-alkyl or C$_1$-C$_4$-alkoxy group.

The diazonium salts of the general formula (V) are known per se, or they can be synthesised by methods which are known per se (Houben-Weyl, Methods of Organic Chemistry, volume X/3).

The agents, according to the invention, for the detection of proteolytic enzymes and, in particular, leucocyte enzymes preferably contain a suitable buffer system. Possible systems for this purpose are, for example, phosphate, borate, carbonate/bicarbonate, carbonate, barbiturate, tris-(hydroxymethyl)-aminomethane (=tris), 2 amino-2-methyl-propane-1,3-diol (=amediol) or aminoacid buffer, the pH value and capacity as a rule being chosen such that a pH value of 6–10, preferably of 7–9, is established in the measurement solution or on the test strip.

The agents according to the invention also preferably contain, in addition to the salts having an accelerating action, further activators, some of which are known per se. Examples of suitable activators are the pyridine derivatives, imidazole compounds, metal complexes and, in particular, alcohols described in European Patent No. A-14,929, n-decanol and, above all, n-undecanol being particularly preferred. Accelerators which were not hitherto known for enzymatic cleavage reactions and which may be mentioned are, moreover, homopolyaminoacids and copolyaminoacids containing basic aminoacids (E. Katchalski and M. Sela in: Advances of Protein Chemistry 13, 243–492 (1958); and C. B. Anfinsen, M. L. Anson, J. T. Edsall and K. Bailey (editors); Academic Press Inc. Publishers, New York, N.Y.) and sequential polyaminoacids, such as are described in a parallel Patent Application. Possible basic aminoacids are those aminoacids which carry amino or guanido groups in the side chains. These are, in particular, lysine and ornithine, as well as arginine, and also basic aminoacids which do not occur in natural proteins, such as, for example, diaminobutyric acid, diaminopropionic acid or diaminopimelic acid. The aminoacids contained in the polyaminoacids can be in racemic form or in the optically active D- or L-form. The molecular weights of the polyaminoacids are between 1,000 and 2,000,000, but preferably between 5,000 and 500,000. The content of basic aminoacids is between 5 and 100 mole %, preferably 20 to 100 mole %, based on the polyaminoacid.

The agents according to the invention can also contain detergents which are known per se, since a more homogeneous colour distribution and a more intensive colouration can thereby be achieved. Both cationic and anionic detergents and also amphoteric nonionic detergents are suitable. Examples which may be mentioned are benzyldimethyl-tetradecyl-ammonium chloride, sodium dodecylsulphate, zephirol, polyvinylpyrrolidone and heparinoid and the polyaminoacids and sequence polymers already mentioned as activators. If appropriate, mixtures of two or more of the abovementioned detergents can also be used.

In the agents according to the invention, the reagents described above are preferably incorporated in an inert carrier of the type which is known per se, particularly preferred carrier matrices being porous materials, such as, in particular, filter paper, and also membranes made of plastic, glass-fibre mats (U.S. Pat. No. 3,846,247), porous ceramic strips, synthetic nonwoven fibres, spongy materials (U.S. Pat. No. 3,552,928), felt, textiles, wood, cellulose or silica gel.

For this purpose, the carriers mentioned are impregnated with a solution of the reagents described above in a suitable solvent which can easily be removed, for example water, methanol, ethanol, acetone, dimethylformamide or dimethylsulphoxide. This is preferably effected in two separate steps: the material is first impregnated with an aqueous solution containing the buffer and other water-soluble additives. It is then impregnated with a solution of the chromogenic enzyme substrates of the general formula (V) and activators. However, the impregnation can also be carried out in another sequence, or with a different composition of the two impregnating solutions. Preferably, the impregnating solution or the fluid to be investigated contains the chromogenic substrate and the diazonium salt in each case in a concentration of $10^{-4}$ to $10^{-1}$ mole/liter, in particular $10^{-3}$ to $10^{-2}$ mole/liter, and the salt in a concentration of 0.01 M to 2 M, in particular 0.1 M to 1 M.

When filter paper is used as the matrix, the finished test papers can be used as such or they can be stuck onto handles in a manner which is known per se or, preferably, sealed between plastics and fine-mesh networks, for example according to DE-OS (German Published Specification) No. 2,118,455.

To produce test strips coated with films, preferably all the reagents are introduced into the solution or dispersion of a film-forming substance, such as, for example, a polyvinyl ester or polyamide, and are homogeneously mixed. A thin layer of the mixture is brushed onto a carrier made of plastic and dried. After drying, the film-coated test strips thus produced are cut and can be used as such or stuck onto handles in a manner which is known per se, or, for example, sealed between plastics and fine-mesh networks according to DE-OS (German Published Specification) No. 2,118,455.

A diagnostic agent according to the invention for the detection of esterolytic and/or proteolytic enzymes, in particular leucocyte enzymes, can be prepared in the form of powder mixtures or reagent tablets by adding the usual pharmaceutical additives to the abovementioned constituents of the test agent and granulating the mixture. Examples of additives of this type are carbohydrates, such as, for example, mono-, oligo- or poly-saccharides, or sugar-alcohols, such as, for example, mannitol, sorbitol or xylitol, or other soluble inert compounds, such as polyethylene glycols or polyvinylpyrrolidone. The powder mixtures or reagent tablets have, for example, a final weight of about 50–200 mg, preferably 50–80 mg.

To prepare lyophilisates with a total weight of in each case about 5–20 mg, preferably about 10 mg, a solution which, in addition to all the reagents required for the test, contains the usual structure-forming agents, such as, for example, polyvinylpyrrolidone, and if appropriate other fillers, such as, for example, mannitol, sorbitol or xylitol, is freeze-dried.

A diagnostic agent according to the invention in the form of a solution preferably contains all the reagents required for the test. Possible solvents are water and mixtures of water with a water-soluble organic solvent, such as, for example, methanol, ethanol, acetone or dimethylformamide. For storage reasons, it may be advantageous to divide the reagents required for the test into two or more solutions, which are only brought together during the actual investigation.

The diagnostic agents thus prepared permit, after immersion in the body fluid to be investigated or after addition to the body fluid in question, rapid and simple detection of the presence of esterolytic and/or proteolytic enzymes, in particular leucocyte enzymes, via colour formation, which can be measured visually or photometrically, for example by reflectance photometry or in a cell. Since the activity of the leucocyte enzymes per cell can be regarded as an essentially constant parameter, the leucocyte concentration of the body fluid investigated can be determined from the intensity of the colour formation. Both intact and lysed leucocytes are thereby recorded with the diagnostic agent according to the invention, since the activity of the leucocyte enzymes is fully retained even after lysis of the leucocytes. Consequently, no lysis error occurs.

The following examples serve to illustrate the present invention. Unless indicated otherwise, the amounts given are to be understood as parts by weight or percentages by weight.

GENERAL PROCEDURE

Depending on the substrate, 50–250 μl of N-methylpyrrolidone were added, as the solubilising agent, to 2.25 ml of the buffer in question, which contains the salt, and the volume of the solution was made up to 2.5 ml with buffer. 5 μl of a solution of 5–100 mg of additional activators, if appropriate, in 1 ml of N-methylpyrrolidone and 5 μl of a solution of 2 mg of sodium dodecylsulphate (SDS) or 4 mg of the other detergents in 1 ml of water or N-methylpyrrolidone were then added to the reaction mixture. After good thorough mixing, 5 μl of a $10^{-1}$ molar substrate solution in N-methylpyrrolidone, dimethylformamide or dimethylsulphoxide were added and, after addition of the leucocyte suspension, the increase in extinction at the stated wavelength was monitored continuously. Spontaneous hydrolysis of the substrate is determined in a parallel batch without the addition of leucocytes with the aid of the increase in extinction.

To determine the rate of reaction, the increase in extinction obtained in the enzyme reaction is reduced by the value determined for spontaneous hydrolysis. Absolute values for cleavage of the substrate (moles×minute$^{-1}$) can be calculated from the extinction differences with the aid of the molar extinction coefficients.

EXAMPLE 1

Filter paper (for example Eaton and Dikeman 205) is impregnated with the following solutions in succession and then dried at 60° C.

Solution 1: 0.1 M tris-(hydroxymethyl)-aminomethane/hydrochloric acid buffer (pH 8.8), containing 0.25 M sodium chloride and 2% of polyvinylpyrrolidone.

Solution 2: $7.5 \times 10^{-3}$ mole/liters of N-tosyl-L-alanine 5-hydroxy-1,2-benzisothiazolyl ester, $10^{-2}$ mole/liters of 2,4-dimethoxybenzenethiazoniumtetrafluoborate and 3.5 g of n-undecanol/liters in anhydrous acetone.

A slightly yellow-coloured test paper which becomes red-brown in colour when immersed in urines containing leucocytes is obtained.

EXAMPLE 2

Filter paper (for example Eaton and Dikeman 205) is impregnated with the following solutions in succession and then dried at 60° C.

Solution 1: 0.1 M borate buffer (pH=9.0), containing 3% of polyvinylpyrrolidone and 0.25 mole of sodium chloride/L.

Solution 2: $5 \times 10^{-3}$ moles/liter of N-tosyl-L-alanine 3-hydroxy-5-phenyl-pyrole ester.

$10^{-2}$ moles/liters of 2-hydroxy-4-sulpho-naphthyldiazoniumtetrafluoborate and 3.5 g of decanol/liters in anhydrous acetone.

A pale yellow-coloured test paper which becomes red to violet in colour when immersed in urines containing leucocytes is obtained.

EXAMPLE 3

Influence of the salt concentration on the cleavage of N-tosyl-L-alanineindoxyl ester in 0.1 M borate buffer (pH 8.8) or 0.1 M tris-(hydroxymethyl)-aminomethane buffer (pH 8.8) with leucocytes with the addition of 10 μg of SDS and 125 μg of n-decanol/test batch.

TABLE 1

| Buffer | Salt | Molarity | relative rate of cleavage |
|---|---|---|---|
| Borate | LiCl | 0.25 | 1.25 |
|  | NaBr | " | 1.15 |
|  | NaCl | " | 1.3 |
|  | NaOCN | " | 1.38 |
|  | Na Phosphate | 0.2 | 3.2 |
|  | NaSCN | 0.25 | 1.42 |
| Tris | — | — | 1 |
|  | Na Borate | 0.1 | 3.15 |
|  | NaCl | 0.1 | 1.0 |
|  | " | 0.25 | 1.5 |
|  | " | 0.5 | 2.3 |
|  | " | 1.0 | 1.75 |
|  | Na Phosphate | 0.2 | 3.25 |
|  | Sodium toluenesulphonate | 0.1 | 1.45 |
|  | " | 0.25 | 1.6 |
|  | " | 0.5 | 1.8 |
|  | Sodium trifluoroacetate | 0.1 | 1.1 |
|  | " | 0.25 | 2.6 |
|  | " | 0.5 | 2.3 |
|  | Magnesium chloride | 0.25 | 1.9 |

EXAMPLE 4

Influence of the salt concentration on the cleavage of N-tosyl-L-alanine indoxyl ester in 0.1M tris-(hydroxymethyl)-aminomethane/hydrochloric acid buffer (pH 8.8) with leucocytes, in the presence of 10 μg of SDS and 125 μg of n-decanol/test batch (determination of cleavage at 360 nm).

TABLE 2

| Salt | Molarity | relative rate of cleavage |
|---|---|---|
| — | — | 1 |
| Sodium acetate | 0.25 | 2.5 |
| " | 0.5 | 2.8 |
| " | 1.0 | 4.2 |
| Sodium succinate | 0.1 | 3.9 |
| " | 0.25 | 4.0 |
| " | 0.5 | 3.7 |
| " | 1.0 | 1.95 |

EXAMPLE 5

Influence of the salt concentration on the cleavage of N-tosyl-L-alanine 3-hydroxy-5-phenyl-pyrrole ester by leucocytes in 0.1 M tris buffer (pH 8.4) in the presence of activators and detergents. (determination of the reaction rate at 330 nm)

TABLE 3

| Molarity (NaCl) | Activator (125 μg/Test) | Detergent | μg/Test | relative rate of cleavage |
|---|---|---|---|---|
| — | n-Decanol | SDS | 10 | 1 |
| 0.1 | " | " | " | 6.35 |
| 0.2 | " | " | " | 13.0 |

TABLE 3-continued

| Molarity (NaCl) | Activator (125 μg/Test) | Detergent | μg/Test | relative rate of cleavage |
|---|---|---|---|---|
| 0.25 | " | " | " | 17.4 |
| 0.3 | " | " | " | 14.6 |
| 0.4 | " | " | " | 7.7 |
| 0.5 | " | " | " | 7.2 |
| 0.25 | — | — | — | 3.2 |
| " | n-Decanol | — | — | 4.6 |
| " | " | SDS | 10 | 16.6 |
| " | n-Undecanol | — | — | 10.3 |
| " | " | SDS | 10 | 22.8 |
| " | " | BDTA | 20 | 5.1 |
| " | " | heparinoid | " | 5.2 |
| " | " | Poly-DL-Lys | " | 8.4 |
| " | n-Dodecanol | SDS | 10 | 18.2 |
| " | " | BDTA | 20 | 4.2 |
| " | " | Heparinoid | " | 3.9 |
| " | n-Tridecanol | SDS | 10 | 15.0 |
| 0.5 | — | — | — | 4.3 |
| " | N—Undecanol | — | — | 10.4 |
| " | " | SDS | 10 | 16.4 |
| " | " | Heparinoid | 20 | 7.8 |
| " | n-Dodecanol | " | " | 6.0 |
| " | n-Tridecanol | " | 20 | 5.4 |

SDS = Sodium dodecyl-sulphate
BDTA = Benzyl-dimethyl-tetradecylamine hydrochloride TABLE 3a

| Salt | Molarity | Activator (125 μg/Test) | Detergent (10 μg/Test) | relative rate of cleavage |
|---|---|---|---|---|
| — | — | n-Decanol | SDS | 1 |
| Na phosphate | 0.25 | n-Undecanol | " | 9.0 |
| Na phosphite | " | " | " | 8.6 |
| Na₂SO₄ | " | " | " | 9.5 |
| KCl | " | " | " | 15.1 |
| MgSO₄ | " | " | " | 9.8 |

EXAMPLE 6

Influence of the sodium chloride concentration on the cleavage of N-tosyl-L-alanine 3-hydroxy-5-phenyl-pyrrole ester in carbonate buffer at pH 8.4 by Leuocoocyte in the presence of various activators and detergents. (Determination of the rate of cleavage at 330 nm). Table 4

TABLE 4

| Buffer | NaCl (moles) | Activator | Detergent | relative weight of cleavage |
|---|---|---|---|---|
| 0.1 M Tris | — | n-Decanol | SDS | 1 |
| 0.1 M Carbonate | — | n-Undecanol | SDS | 5.8 |
| | — | " | Hep. | 6.2 |
| | — | " | BDTA/SDS | 8.4 |
| | — | " | BDTA/Hep. | 6.8 |
| | 0.25 | " | SDS | 24.5 |
| | " | " | BDTA | 6.5 |
| | " | " | Hep. | 16.8 |
| | 0.25 | " | BDTA/SDS | 19.5 |
| | " | " | BDTA/Hep. | 20.1 |

SDS = Sodium dodecyl-sulphate (10 μg/test)
BDTA = Benzyl-dimethyl-tetradecylamine hydrochloride (20 μg/test)
Hep = Heparinoid (20 μg/test)

EXAMPLE 8

Influence of the salt content on the cleavage of N-tosyl-L-alanine 3-hydroxy-5-phenyl-pyrrole ester in 0.1 M borate buffer, pH 8.4, by leucocytes in the presence of undecanol as the accelerator and SDS as the detergent (determination of the rate of cleavage at 320 nm).

TABLE 5

| Salt | Molarity | relative rate of cleavage |
|---|---|---|
| LiBr | 0.1 | 1.5 |
| NaBr | " | 1.8 |
| KBr | " | 1.1 |
| LiCl | 0.25 | 1.55 |
| NaCl | " | 1.85 |
| KCl | " | 2.05 |
| NH₄Cl | 0.1 | 1.4 |
| NaF | " | 1.15 |
| KF | " | 1.5 |
| Sodium glycerophosphate | " | 1.35 |
| Sodium phosphite | " | 2.05 |
| Na₂SO₄ | 0.05 | 1.9 |
| " | 0.1 | 2.3 |
| " | 0.15 | 2.4 |
| " | 0.2 | 2.8 |
| " | 0.25 | 2.6 |
| " | 0.3 | 2.1 |
| K₂SO₄ | 0.1 | 2.05 |
| " | 0.15 | 2.35 |
| " | 0.2 | 2.05 |
| " | 0.25 | 1.1 |
| Na₂S₂O₃ | 0.02 | 1.9 |
| " | 0.05 | 2.35 |
| " | 0.075 | 2.5 |
| " | 0.1 | 2.9 |
| " | 0.125 | 2.35 |
| Sodium succinate | 0.1 | 1.15 |
| Sodium galactate | 0.1 | 1.15 |
| Sodium galacturonate | 0.05 | 1.2 |
| | 0.1 | 1.4 |
| | 0.2 | 1.45 |
| Potassium gluconate | 0.05 | 1.2 |
| | 0.1 | 1.6 |
| | 0.2 | 1.5 |
| Sodium glucuronate | 0.1 | 1.3 |
| Sodium tartrate | 0.05 | 1.2 |
| | 0.1 | 1.4 |
| | 0.2 | 1.4 |

General Operating Instructions for the Preparation of the N-tosyl-L-alanyl Esters The esters were in each case prepared by reacting N-tosyl-L-alanyl chloride with the phenols in absolute methyl ethyl ketone or absolute toluene in the presence of powdered potassium carbonate. After stirring at about 55° C. for 6 to 12 hours, between 40 and 70% of the phenol had reacted. The molar ratio of phenol:K₂CO₃ acid chloride was usually 1:1.5:1.5. The pH value was about 7 throughout the entire reaction time. For working up, the potassium carbonate was filtered off at 50° C. and the solvent was then distilled off in vacuo. The product was purified via column chromatography with silica gel-eluant (petroleum ether:acetone=about 9:1) and subsequent recrystallisation.

L-p-tosylalanine

Literature: E. Fischer and W. Lipschitz, B. 48, 362 (1915).

83.7 g (0.93 mole) of L-alanine are dissolved in 465 ml of approximately 2 N sodium hydroxide solution. 186 g (0.976 mole) of p-toluenesulphonyl chloride are added to the solution in portions at 70°–72° C. in the course of 20 minutes. During the addition of the sulphonyl chloride, the reaction mixture is kept at pH 10 with approximately 2 N sodium hydroxide solution by means of an automatic titrator; 560 ml of 2 N sodium hydroxide solution are consumed here. When the pH of the reaction mixture no longer changes, the mixture is cooled to 15°–5° C. and brought to pH 3 with 37% strength hydrochloric acid. The product which has separated out is filtered off with suction and the moist filter cake is recrystallised from 2,350 ml of water.

Yield: 185.5 g (82% of theory) of L-p-tosylalanine of melting point 132°–135° C.

p-Tosyl-L-alanyl chloride 158.1 g (0.65 mole) of L-p-tosylalanine are stirred in 350 ml of thionyl chloride at 40° C., until a clear solution has formed. The excess thionyl chloride is then distilled off under a waterpump vacuum. The residue in the flask is taken up in 300 ml of distilled toluene. A clear, slightly yellowish solution is obtained, which is poured into 900 ml of stirred naphtha. The acid chloride precipitates. The following day, it is filtered off with suction, washed with light gasolene and dried in a vacuum desiccator over calcium chloride/potassium hydroxide.

Yield: 155 g (91% of theory) of almost colourless crystals of melting point 81°–83° C.

What is claimed is:

1. Agent for the detection of esterolytic or proteolytic enzymes, containing (a) an aminoacid ester or peptide ester of a phenol, as the chromogenic enzyme substrate, and (b) from (b) 0.05 M to 2 M of a substance which accelerates the enzymatic cleavage of the aminoacid ester or peptide ester bond of component (a), wherein said substance is a salt having a cation selected from the group consisting of Li+, Na+, K+ and Mg++ and an anion selected from the group consisting of halide, pseudohalide, sulphate, phosphate, acetate, trifluoroacetate, sulphonate and succinate.

2. Agent according to claim 1 wherein it contains a polyaminoacid with a molecular weight of between 1,000 and 2,000,000 as an additional accelerating substance.

3. Agent according to claim 2, wherein the polyaminoacid is built up from only one aminoacid, from two or more different aminoacids in random sequence, or from two or more different aminoacids with a recurring aminoacid sequence.

4. Agent according to claim 3, wherein the polyaminoacid is built up from aminoacids of the general formula

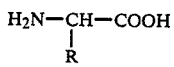

in which R is hydrogen or a branched alkyl, cycloalkyl or aralkyl radical which has 1 to 15 carbon atoms and which may be substituted by 1 or 2 hydroxyl, mercapto, carboxyl, amino or guanido groups.

5. Agent according to claim 3, wherein 5 to 100 mole % of the aminoacid units of the polyaminoacid carry a basic group.

6. Agent according to claim 1, wherein in that the agent is incorporated in an inert carrier.

7. Process for the detection of esterolytic or proteolytic enzymes in a liquid sample wherein the liquid sample is brought into contact with an agent according to claim 1 or 6 and the color reaction which occurs is determined.

* * * * *